United States Patent
Wiederin et al.

(10) Patent No.: US 9,138,657 B1
(45) Date of Patent: Sep. 22, 2015

(54) FRACTIONAL-VOLATILIZATION SEPARATOR

(75) Inventors: Daniel R. Wiederin, Omaha, NE (US); Austin Schultz, Omaha, NE (US)

(73) Assignee: Elemental Scientific, Inc., Omaha, NE (US)

(*) Notice: Subject to any disclaimer, the term of this patent is extended or adjusted under 35 U.S.C. 154(b) by 147 days.

(21) Appl. No.: 13/560,198

(22) Filed: Jul. 27, 2012

Related U.S. Application Data

(60) Provisional application No. 61/512,465, filed on Jul. 28, 2011.

(51) Int. Cl.
- *B01D 3/34* (2006.01)
- *G01N 30/12* (2006.01)
- *B01D 3/02* (2006.01)
- *B01D 3/00* (2006.01)
- *B01D 1/30* (2006.01)
- *B01D 19/00* (2006.01)
- *G01N 1/40* (2006.01)

(52) U.S. Cl.
CPC *B01D 3/343* (2013.01); *B01D 1/30* (2013.01); *B01D 3/008* (2013.01); *B01D 3/02* (2013.01); *B01D 19/0021* (2013.01); *G01N 2001/4027* (2013.01); *G01N 2030/126* (2013.01)

(58) Field of Classification Search
CPC ............ B01D 1/30; B01D 3/008; B01D 3/02; B01D 3/343; B01D 19/005; B01D 19/0021; B01D 2221/01; G01N 2001/4027; G01N 2030/126
USPC .................. 202/163, 164, 176, 232, 257, 262, 202/267.1; 203/49, 86, 90; 261/4, 37, 74, 261/108, 112.1; 95/155, 181, 204; 96/156; 73/863.21

See application file for complete search history.

(56) References Cited

U.S. PATENT DOCUMENTS

| | | | | |
|---|---|---|---|---|
| 3,822,192 A * | 7/1974 | Brown | ................................ | 3/49 |
| 3,969,196 A * | 7/1976 | Zosel | ............................... | 203/49 |
| 4,559,808 A * | 12/1985 | Sturman | ........................ | 73/19.01 |
| 5,454,860 A * | 10/1995 | Zhu | .................... | 96/202 |
| 5,792,663 A | 8/1998 | Fry et al. | .......................... | 436/73 |
| 5,939,648 A * | 8/1999 | Phan | ........................ | 73/864.81 |
| 6,911,121 B1 * | 6/2005 | Beckman | ........................ | 203/49 |
| 6,919,000 B2 * | 7/2005 | Klausner et al. | ................ | 203/10 |
| 7,552,617 B2 * | 6/2009 | Danilchik | .................... | 73/23.41 |
| 7,931,782 B2 * | 4/2011 | Torii et al. | .......................... | 201/1 |
| 8,297,135 B2 * | 10/2012 | Trapp | .............................. | 73/866 |
| 8,408,044 B2 * | 4/2013 | Danilchik | .................... | 73/23.41 |
| 8,647,477 B2 * | 2/2014 | Govindan et al. | ................ | 203/11 |
| 2005/0230238 A1 * | 10/2005 | Klausner et al. | ................ | 203/10 |
| 2007/0137996 A1 * | 6/2007 | Beckman | ........................ | 202/158 |

* cited by examiner

*Primary Examiner* — In Suk Bullock
*Assistant Examiner* — Jonathan Miller
(74) *Attorney, Agent, or Firm* — Advent, LLP

(57) ABSTRACT

A fractional-volatilization separator includes a liquid inlet port for receiving a liquid mixture and a liquid waste outlet port for draining the liquid mixture. The fractional-volatilization separator includes a separator body having an interior wall portion connecting the liquid inlet port and the liquid waste outlet port. The fractional-volatilization separator includes a carrier gas inlet port coupled with the separator body for receiving a carrier gas, and a carrier gas outlet port coupled with the separator body for expelling the carrier gas. The interior wall portion is configured to cause the liquid mixture to flow from the liquid inlet port across the interior wall portion to the liquid waste outlet port to enhance evaporation of a first component part from a second component part of the liquid mixture as the carrier gas flows from the carrier gas inlet port to the carrier gas outlet port.

14 Claims, 8 Drawing Sheets

FRACTIONAL-VOLATILIZATION SEPARATOR

CROSS-REFERENCE TO RELATED APPLICATIONS

The present application claims the benefit of 35 U.S.C. §119(e) of U.S. Provisional Application Ser. No. 61/512,465, filed Jul. 28, 2011, and titled "FRACTIONAL-VOLATILIZATION SEPARATOR," which is herein incorporated by reference in its entirety.

BACKGROUND

Fractional distillation may be used to separate a sample mixture into its component parts (fractions). One technique for performing fractional distillation employs a boiling pot and a condenser to heat a sample mixture so that a more volatile component will concentrate to a greater degree in the vapor leaving the mixture. Another distillation technique bubbles a gas through a liquid mixture, causing components to evaporate from the mixture. Rotary evaporators may also be used to increase the surface area of a liquid mixture as a flow of gas is directed onto the mixture. However, these techniques may be difficult to implement with continuous flow-through applications, where it may be necessary to clean equipment when sample mixtures are changed.

SUMMARY

A fractional-volatilization separator configured to separate a sample mixture into its component parts (fractions) is described. In one or more implementations, the fractional-volatilization separator includes a liquid inlet port for receiving a liquid mixture. The liquid mixture contains a first component part and a second component part. The fractional-volatilization separator also includes a liquid waste outlet port for draining the liquid mixture after the first component part has been at least partially separated from the second component part of the liquid mixture. The fractional-volatilization separator includes a separator body having an interior wall portion connecting the liquid inlet port and the liquid waste outlet port. The interior wall portion defines a generally longitudinal interior cavity. The fractional-volatilization separator further includes a carrier gas inlet port and a carrier gas outlet port. The carrier gas inlet port is coupled with the separator body and connected to the generally longitudinal interior cavity proximal to the liquid waste outlet port and distal from the liquid inlet port for receiving a carrier gas. The carrier gas outlet port is coupled with the separator body and connected to the generally longitudinal interior cavity proximal to the liquid inlet port and distal from the liquid waste outlet port for expelling the carrier gas.

The interior wall portion is configured to cause a liquid mixture introduced at the liquid inlet port to flow from the liquid inlet port, evenly distribute (spread) across the interior wall portion, and flow to the liquid waste outlet port when the generally longitudinal interior cavity is oriented in at least a substantially vertical orientation. The evaporation of a component part from the liquid mixture is enhanced by increasing the surface area of the liquid mixture as it spreads across the interior wall portion of the separator body in the presence of the carrier gas. Thus, the interior wall portion may be constructed to cause the liquid mixture introduced at the liquid inlet port to adhere to the interior wall portion.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Figure 1:
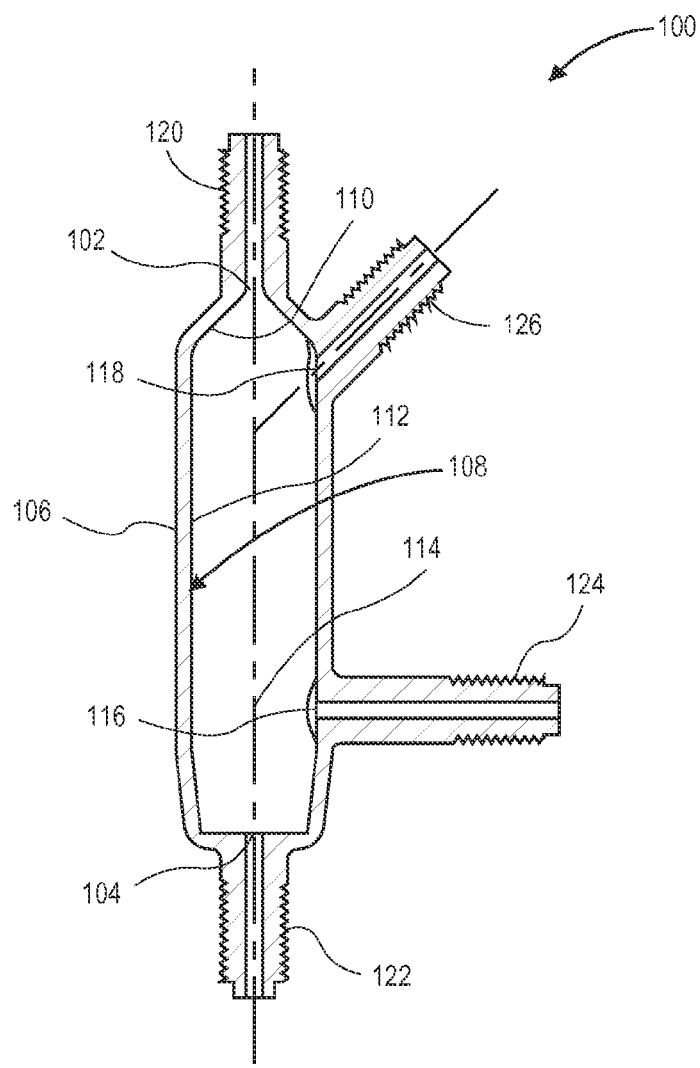
FIG. 1 is a cross-sectional side elevation view of a fractional-volatilization separator in accordance with an example implementation of the present disclosure.
Figure 2:
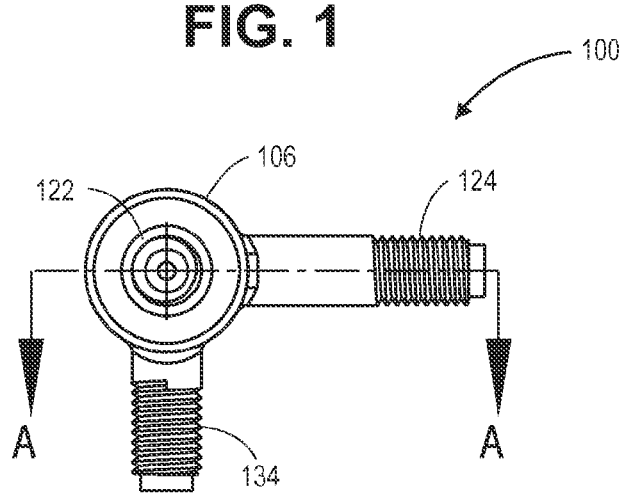
FIG. 2 is a bottom plan view of the fractional-volatilization separator illustrated in FIG. 1, where section line A-A indicates the direction of the cross-section of FIG. 1.
Figure 3:
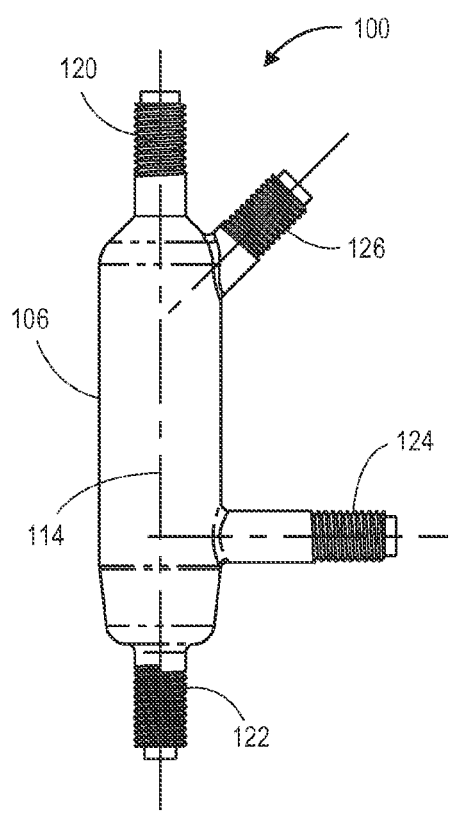
FIG. 3 is a side elevation view of the fractional-volatilization separator illustrated in FIG. 1.
Figure 4:
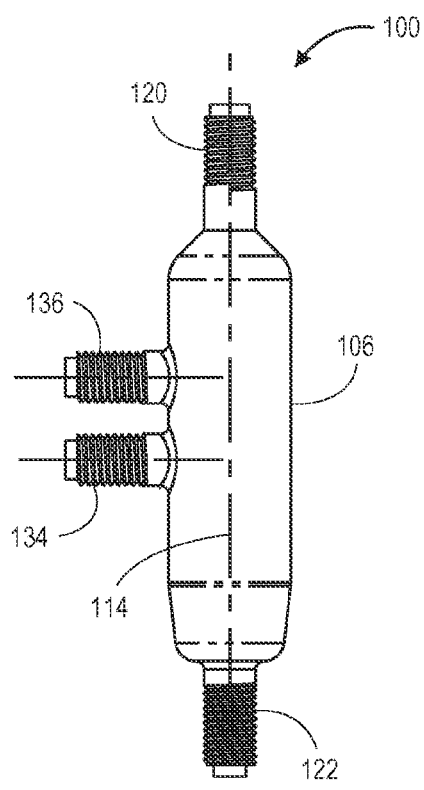
FIG. 4 is a front elevation view of the fractional-volatilization separator illustrated in FIG. 1.
Figure 5:
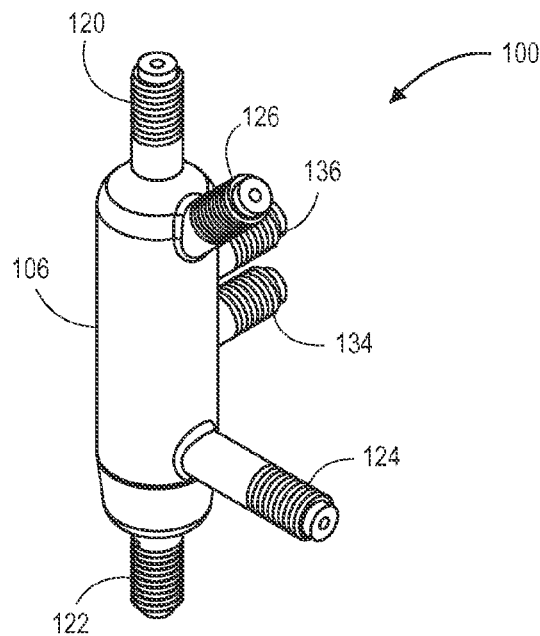
FIG. 5 is an isometric view of the fractional-volatilization separator illustrated in FIG. 1.

Fractional-volatilization separation may be used to separate a more volatile component from a less volatile component of a sample material. This may be desirable when it is necessary to detect a small amount of a component in a material mixture, such as for mass spectrometry, and so forth. Previous fractional-volatilization systems have employed techniques for increasing the surface area of a sample material in the presence of a carrier gas, to enhance the separation of components from the material. However, such systems have either been limited to batch processing or have been prohibitively expensive and/or complicated to manufacture. One type of component separation technique uses a vertically oriented separator having a housing with an upwardly directed post protruding from the bottom of the housing into the center of the separator. In this configuration, a stream of a liquid mixture is poured onto the post, so that components may be evaporated out of the mixture in the presence of a carrier gas introduced into the housing. The protruding post serves to increase the surface area of the liquid as it spreads across the post and flows to the bottom of the housing. However, because it is desirable to form the housing and the post together as a single piece, it is difficult and expensive to construct such a separator.

Accordingly, the present disclosure is directed to a fractional-volatilization Gas-Liquid Separator (GLS) that may be easily manufactured from blown quartz, or the like. The fractional-volatilization separator may be suitable for use in a system for performing hydride generation (e.g., for mass spectrometry). The fractional-volatilization separator includes a liquid inlet port and a liquid waste outlet port. The liquid inlet port is oriented at or near the top of the fractional-volatilization separator for receiving a liquid mixture, while the liquid waste outlet port is oriented at or near the bottom of the fractional-volatilization separator for draining the liquid mixture after a first component part has been at least partially separated from a second component part of the liquid mixture. The fractional-volatilization separator includes a separator body having an interior wall portion connecting the liquid inlet port and the liquid waste outlet port. The interior wall portion may be frosted quartz.

The fractional-volatilization separator includes a carrier gas inlet port and a carrier gas outlet port. The carrier gas inlet port is connected to the separator body for receiving a carrier gas. The carrier gas outlet port is connected to the separator body for expelling the carrier gas. The liquid inlet port, the liquid waste outlet port, the carrier gas inlet port, and/or the carrier gas outlet port may extend through couplings, which may include threads for connecting to threaded connectors of supply tubes, or the like. The fractional-volatilization separator may include one or more support attachment points for supporting the separator body. In implementations, the support attachment points may be threaded for connecting to threaded support structures. In implementations, the liquid inlet port, the liquid waste outlet port, the separator body, the carrier gas inlet port, and the carrier gas outlet port may be blown from quartz as a single piece.

In the following discussion, example implementations of fractional-volatilization separators that include a longitudinal interior cavity for increasing the surface area of a liquid mixture in the presence of a carrier gas are first described.

Example Implementations

FIGS. 1 through 6D illustrate a fractional-volatilization separator 100 in accordance with example implementations of the present disclosure. As shown, the fractional-volatilization separator 100 includes a liquid inlet port 102 for receiving a liquid mixture. In implementations, the liquid mixture may include various formulations of liquid and possibly gas components. For example, the liquid mixture may comprise a mixture of liquid and gas, two or more liquids having different vapor pressures, and other component combinations. When the fractional-volatilization separator 100 is oriented in a substantially vertical upright position (e.g., as illustrated in FIG. 1), the liquid inlet port 102 is oriented at or near the top of the fractional-volatilization separator 100. The fractional-volatilization separator 100 also includes a liquid waste outlet port 104 for draining the liquid mixture (e.g., after a first component part has been separated from a second component part of the liquid mixture). When the fractional-volatilization separator 100 is oriented in the upright position, the liquid waste outlet port 104 is oriented at or near the bottom of the fractional-volatilization separator 100.

The fractional-volatilization separator 100 includes a separator body 106 having an interior wall portion 108 connecting the liquid inlet port 102 and the liquid waste outlet port 104. In implementations, the interior wall portion 108 defines a generally longitudinal interior cavity having a first region 110 adjacent to the liquid inlet port 102 and a second region 112 adjacent to the liquid waste outlet port 104. For example, the generally longitudinal interior cavity may extend generally along a longitudinal axis 114 of the separator body 106. In implementations, the generally longitudinal interior cavity of the separator body 106 is configured so that a liquid mixture introduced at the liquid inlet port 102 will be evenly distributed/spread across the interior wall portion 108 and flow to the liquid waste outlet port 104.

The fractional-volatilization separator 100 includes a carrier gas inlet port 116 for receiving a carrier gas, or the like. The carrier gas inlet port 116 is connected to the separator body 106 for fluid communication with the generally longitudinal interior cavity of the separator body 106. In some implementations, when the fractional-volatilization separator 100 is oriented in the upright position illustrated in FIG. 1, the carrier gas inlet port 116 is oriented at or near the bottom of the fractional-volatilization separator 100. For example, the carrier gas inlet port 116 may be connected to the separator body 106 at or near the liquid waste outlet port 104. However, in other implementations, the carrier gas inlet port 116 may be connected to the separator body 106 in other orientations, such as positioned near the liquid inlet port 102. The fractional-volatilization separator 100 includes a carrier gas outlet port 118 for expelling the carrier gas. The carrier gas outlet port 118 is also connected to the separator body 106 for fluid communication with the generally longitudinal interior cavity of the separator body 106. In some implementations, when the fractional-volatilization separator 100 is oriented in the upright position, as illustrated in FIG. 1, the carrier gas outlet port 118 is oriented near the top of the fractional-volatilization separator 100. For example, the carrier gas outlet port 118 may be connected to the separator body 106 near the liquid inlet port 102. In other implementations, the carrier gas outlet port 118 may be connected to the separator body 106 in other orientations, such as positioned near the liquid waste outlet port 104.

In implementations, the carrier gas outlet port 118 may be oriented upwardly at an angle from the horizontal (e.g., for preventing liquid waste from the liquid mixture from entering the stream of carrier gas expelled at the carrier gas outlet port 118). For example, the carrier gas outlet port 118 may be oriented upwardly at an angle of approximately forty-five degrees (45°) from the horizontal. However, this angle is provided by way of example only, and it should be noted that the carrier gas outlet port 118 may be oriented at a number of different angles. In some implementations, the liquid inlet port 102, the liquid waste outlet port 104, the separator body 106, the carrier gas inlet port 116, and the carrier gas outlet port 118 may be glass blown from quartz. Further, the interior wall portion 108 may be frosted in this type of implementation to enhance the evaporation of components of the liquid mixture into the carrier gas by increasing the surface area of the interior wall portion 108. In other implementations, the fractional-volatilization separator 100 may be constructed from other materials. For example, the liquid inlet port 102, the liquid waste outlet port 104, the separator body 106, the carrier gas inlet port 116, and the carrier gas outlet port 118 may be formed from glass, polyether ether ketone (PEEK), Lexan polycarbonate acrylic, and various mixtures of plastic and other compounds, such as plastic and hydrofluoric acid. However, this list is provided by way of example and is not meant to be restrictive of the present disclosure. Thus, other materials may be used to construct the fractional-volatilization separator 100.

In example implementations, the liquid inlet port 102 may extend through a coupling 120. The coupling 120 may be connectable to a source of liquid mixture, such as a liquid supply tube having a threaded connecter, or the like. In implementations, the coupling 120 may include threads for connecting with a threaded connector. In other implementations, the coupling 120 may include other connecting features, such as quick connect coupling hardware, or the like. The liquid waste outlet port 104 may extend through a coupling 122, while the carrier gas inlet port 116 may extend through a coupling 124, and the carrier gas outlet port 118 may extend through a coupling 126. The couplings 122, 124, and/or 126 may be configured in a similar manner to the coupling 120. For example, the coupling 122 may include threads for connecting to a threaded connector of a tube for receiving the liquid mixture. The coupling 124 may include threads for connecting to a threaded connector of a tube for supplying the carrier gas, while the coupling 126 may include threads for connecting to a threaded connector of a tube for receiving the carrier gas.

Referring now to FIGS. 6A through 6D, the liquid inlet port 102 defines an aperture having a first diameter $D_1$. The second region 112 of the interior wall portion 108 has a second diameter $D_2$. In implementations, the first region 110 of the interior wall portion 108 transitions from the first diameter $D_1$ of the liquid inlet port 102 to the second diameter $D_2$ of the interior wall portion 108. The first interior wall portion 108 is configured to cause a liquid mixture introduced at the liquid inlet port 102 to flow from the liquid inlet port 102, spread across the interior wall portion 108, and collect at the liquid waste outlet port 104 when the generally longitudinal interior cavity is oriented in an upright position. Thus, the configuration of the interior wall portion 108 is designed to enhance evaporation of a first component part from a second component part of a liquid mixture as a carrier gas flows from the carrier gas inlet port 116 to the carrier gas outlet port 118 across the mixture.

The evaporation of the first component part from the liquid mixture is enhanced by increasing the surface area of the liquid mixture as it coats the interior wall portion 108 in the presence of the carrier gas. Thus, the interior wall portion 108 is constructed to cause the liquid mixture introduced at the liquid inlet port 102 to adhere to the interior wall portion 108. For example, the first region 110 of the interior wall portion 108 may be oriented at an angle A from the horizontal, as illustrated in FIGS. 6A through 6D. In some implementations, angle A may be approximately forty-five degrees (45°). However, in other implementations, different angles may be employed. For instance, angle A may be between at least approximately thirty degrees) (30°) and at least approximately sixty degrees)(60°).

Figure 6A:
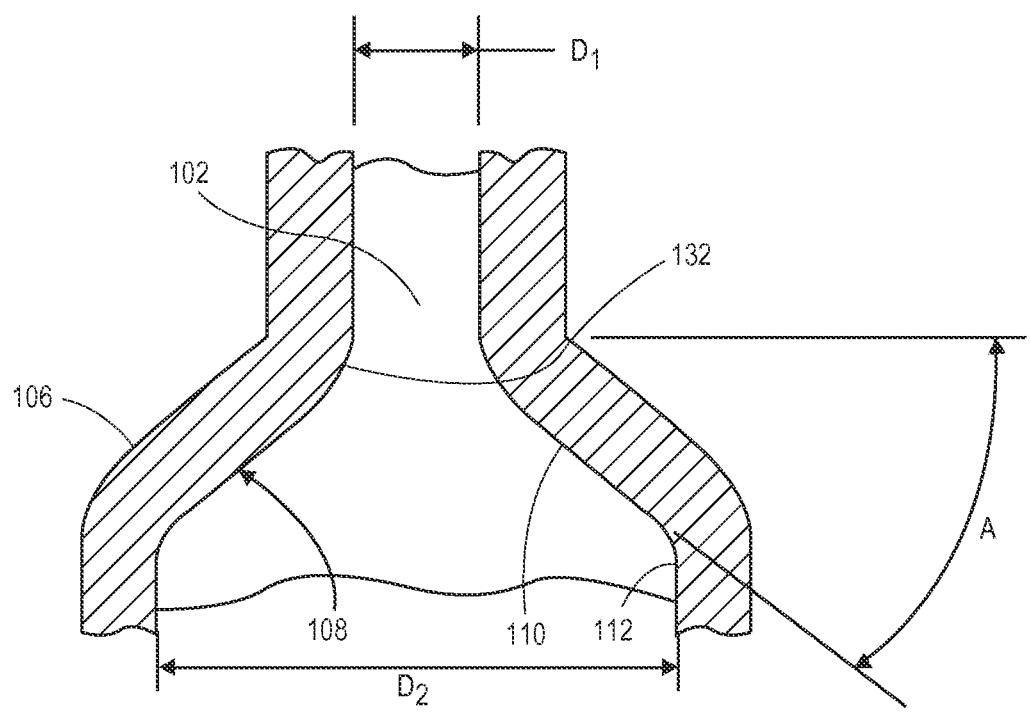
FIG. 6A is a partial cross-sectional side elevation view of the fractional-volatilization separator illustrated in FIG. 1.
Figure 6B:
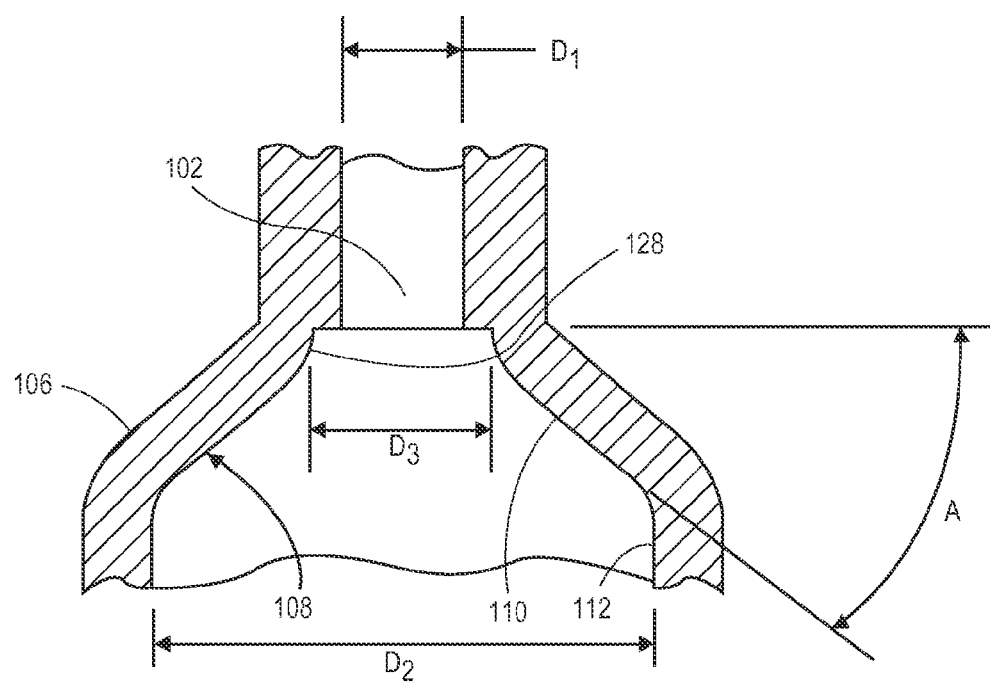
FIG. 6B is a partial cross-sectional side elevation view illustrating another fractional-volatilization separator in accordance with an example implementation of the present disclosure.
Figure 6C:
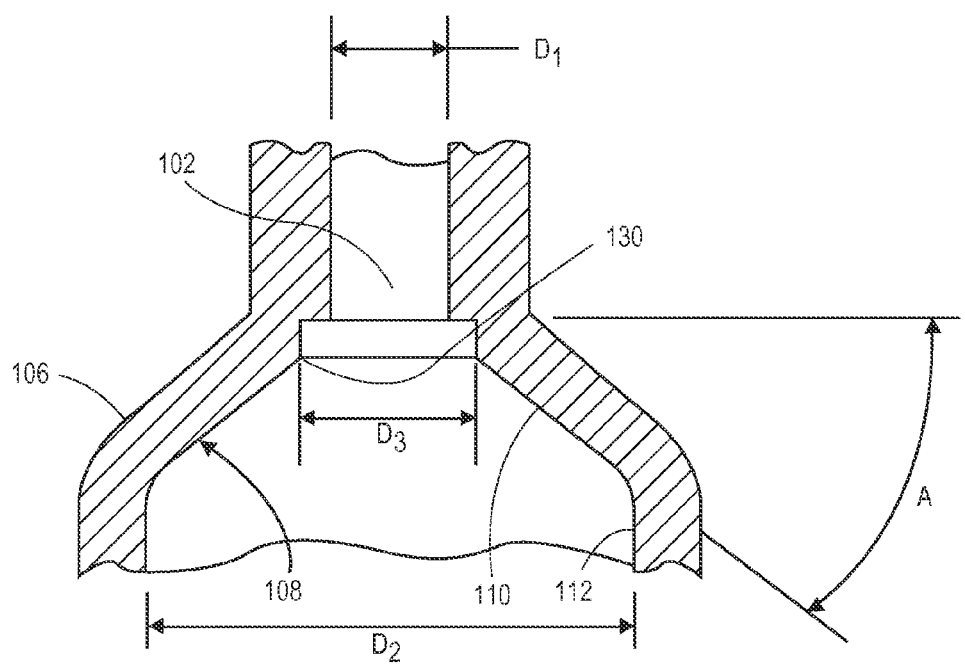
FIG. 6C is a partial cross-sectional side elevation view illustrating a further fractional-volatilization separator in accordance with an example implementation of the present disclosure.
Figure 6D:
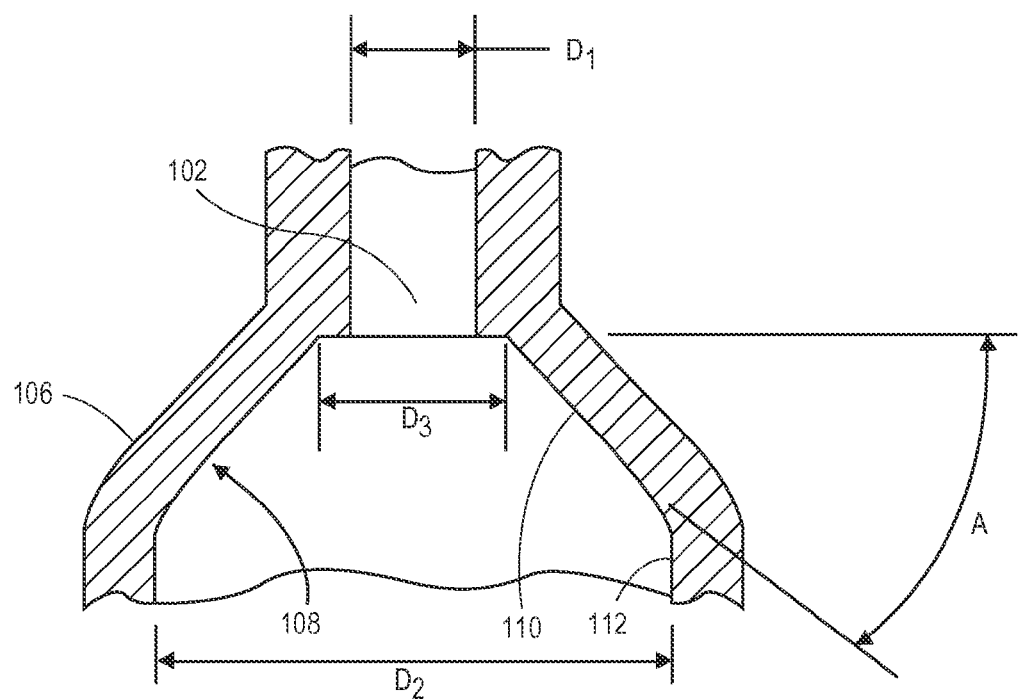
FIG. 6D is a partial cross-sectional side elevation view illustrating another fractional-volatilization separator in accordance with an example implementation of the present disclosure.

In an implementation described in FIG. 6A, the first diameter $D_1$ may transition to the second diameter $D_2$ via a curved transition 132. In the implementations described in FIGS. 6B through 6D, the first region 110 transitions from the first diameter $D_1$ to a third diameter $D_3$ across a substantially horizontal plane, and then from the third diameter $D_3$ to the second diameter $D_2$. In the implementation described in FIG. 6B, the cross-sectional profile of the interior wall portion 108 includes a curved transition 128 from the third diameter $D_3$ to the second diameter $D_2$. In another implementation described in FIG. 6C, the cross-sectional profile of the interior wall portion 108 includes an angled transition 130 from the third diameter $D_3$ to the second diameter $D_2$. The cross-sectional profile may also transition directly from the third diameter $D_3$ to the second diameter $D_2$, as illustrated in FIG. 6D. In other implementations, the first diameter $D_1$ may transition to the second diameter $D_2$ along different cross-sectional geometries. The transitions described in the accompanying figures are provided by way of example only and are not meant to be restrictive. Thus, other transition profiles may be employed having other various shapes for causing the liquid mixture to spread across the interior wall portion 108, including convex curves, concave curves, angled transitions and the like.

The fractional-volatilization separator 100 may include a mounting structure for mounting the separator 100 to a supporting structure, such as a support stand or housing. For example, in the implementation shown, the fractional-volatilization separator 100 is illustrated as including a first support attachment point 134 and possibly a second support attachment point 136 connected to the separator body 106 for supporting the separator body 106. In implementations, the first support attachment point 134 and/or the second support attachment point 136 may be threaded for connecting to threaded support structures. In other implementations, the first support attachment point 134 and/or the second support attachment point 136 may include other connecting features, such as quick connect coupling hardware, or the like.

Figure 7:
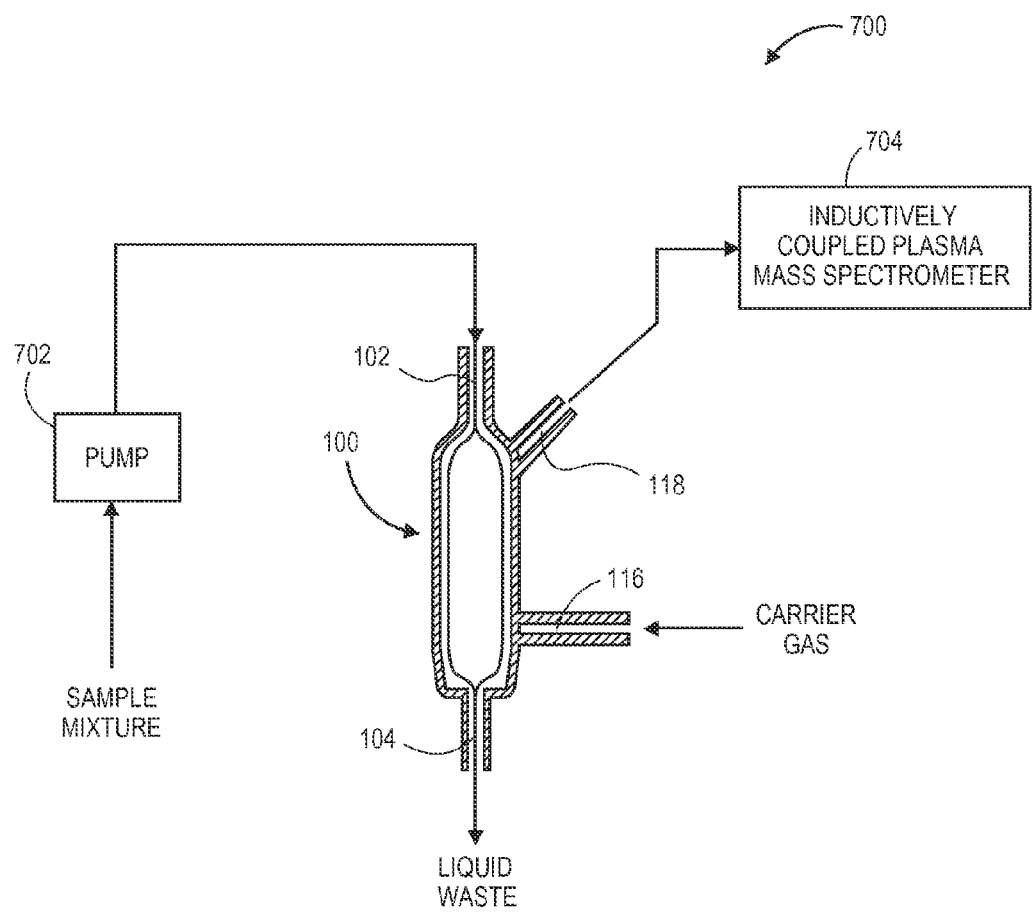
FIG. 7 is a schematic illustrating a mass spectrometer system utilizing a fractional-volatilization separator in accordance with an example implementation of the present disclosure.

FIG. 7 illustrates a system 700 in accordance with example implementations of the present disclosure for detecting one or more components in a liquid mixture. As shown, the system 700 includes a fractional-volatilization separator 100 having a liquid inlet port 102 for receiving a sample mixture, a liquid waste outlet port 104 for draining the sample mixture, a carrier gas inlet port 116 for receiving a carrier gas, and a carrier gas outlet port 118 for expelling the carrier gas, where the sample mixture is distributed across an interior wall portion connecting the liquid inlet port 102 and the liquid waste outlet port 104 in the presence of the carrier gas (e.g., as previously described). The fractional-volatilization separator 100 may be connected to a pump 702 (e.g., a peristaltic pump) for pumping the sample mixture to the liquid inlet port 102. The fractional-volatilization separator 100 may also be connected to a mass spectrometer, such as an inductively coupled plasma mass spectrometer (ICP-MS) 704, or the like.

In implementations, the system 700 may be employed to detect hydride forming elements, such as Arsenic (As), Selenium (Se), and/or Antimony (Sb). For example, hydrides from a sample mixture may be separated from liquid waste, and then carried to an ICP-MS 704 injector in gaseous form, where the hydrides may be detected. The expelled carrier gas may be supplied to a spray chamber and/or a torch. In example implementations, the carrier gas may be Argon (Ar). However, it is should be noted that the above-referenced hydride forming elements, and/or carrier gas are provided by way of example only, and are not meant to be restrictive of the present disclosure. Thus, other various mixtures and components may be used with the system 700, including other hydride forming compounds, and the like.

Figure 8:
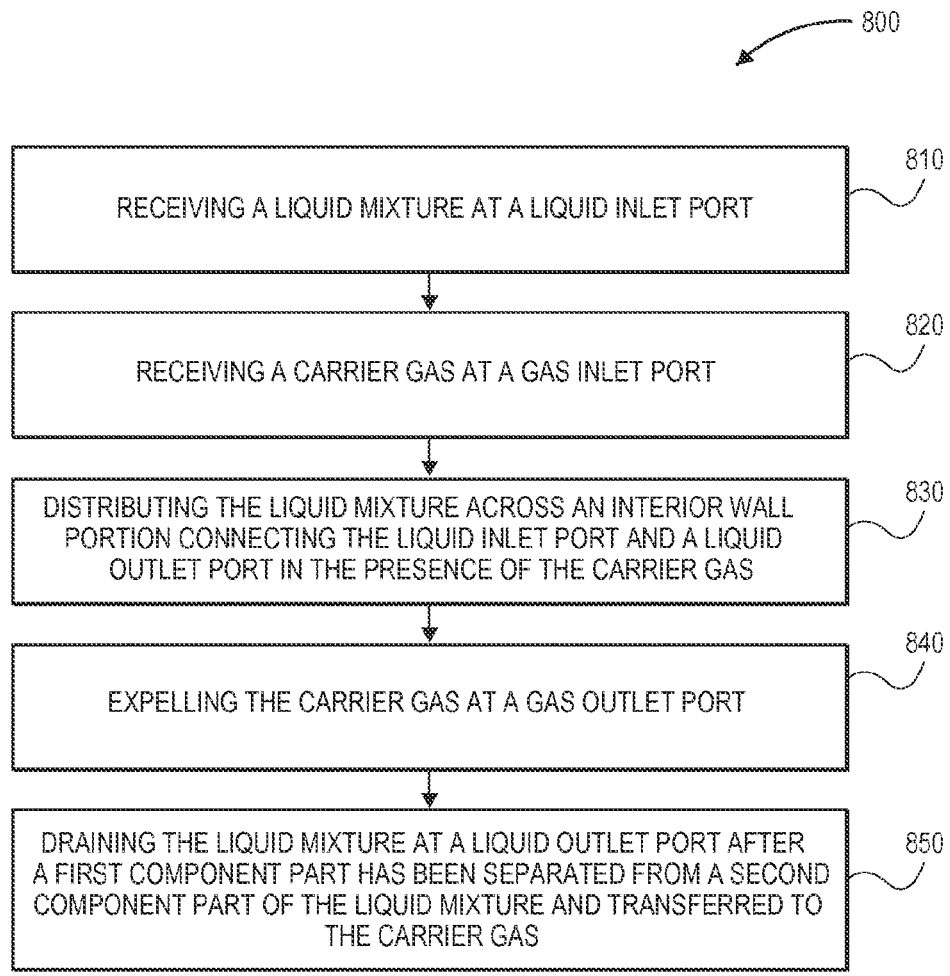
FIG. 8 is a flow diagram illustrating a method for separating a first component part from a second component part of a liquid mixture in accordance with an example implementation of the present disclosure, where the mixture is spread across an interior wall portion of a fractional-volatilization separator body in the presence of a carrier gas.

Referring now to FIG. 8, a method 800 for separating a first component part from a second component part of a liquid mixture is described. In accordance with the method 800, a liquid mixture is received at a liquid inlet port (Block 810). A carrier gas is received at a carrier gas inlet port (Block 820). The liquid mixture is distributed across an interior wall portion connecting the liquid inlet port and a liquid waste outlet port in the presence of the carrier gas (Block 830). For example, with reference to the fractional-volatilization separator 100 described above, a sample mixture may be introduced at the liquid inlet port 102, spread across the interior wall portion 108, and collected at the liquid waste outlet port 104. As described, the configuration of the interior wall portion 108 is designed to enhance evaporation of a first component part from a second component part of the sample mixture as a carrier gas flows from the carrier gas inlet port 116 to the carrier gas outlet port 118 across the mixture. The carrier gas is expelled at a carrier gas outlet port (Block 840). The liquid mixture is drained at a liquid waste outlet port after a first component part has been separated from a second component part of the liquid mixture and transferred to the carrier gas (Block 850).

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A fractional-volatilization separator comprising:
   a liquid inlet port for receiving a liquid mixture, the liquid mixture containing a first component part and a second component part;
   a liquid waste outlet port for draining the liquid mixture after the first component part has been at least partially separated from the second component part of the liquid mixture;
   a separator body having an interior wall portion connecting the liquid inlet port and the liquid waste outlet port, the interior wall portion defining a generally longitudinal interior cavity and an aperture having a first diameter proximate to the liquid inlet port, the interior wall portion having a second diameter below the aperture when the fractional-volatilization separator is in an upright position, the interior wall portion transitioning outwardly from the first diameter to the second diameter at an angle;
   a carrier gas inlet port coupled with the separator body and connected to the generally longitudinal interior cavity for receiving a carrier gas; and
   a carrier gas outlet port coupled with the separator body and connected to the generally longitudinal interior cavity for expelling the carrier gas, the interior wall portion configured to cause the liquid mixture to flow from the liquid inlet port across the interior wall portion to the liquid waste outlet port to enhance evaporation of the first component part from the second component part as the carrier gas flows from the carrier gas inlet port to the carrier gas outlet port.

2. The fractional-volatilization separator as recited in claim 1, wherein a first region of the interior wall portion disposed between the first diameter and the second diameter is oriented at an angle of between thirty degrees (30°) and sixty degrees (60°) from the horizontal when the generally longitudinal interior cavity is oriented in the upright position.

3. The fractional-volatilization separator as recited in claim 1, wherein the liquid mixture comprises a mixture of at least one of a liquid and a gas, or a first liquid and a second liquid having different vapor pressures.

4. The fractional-volatilization separator as recited in claim 1, further comprising:
   a first support attachment point connected to the separator body for coupling with a support for supporting the fractional-volatilization separator.

5. The fractional-volatilization separator as recited in claim 1, wherein the liquid inlet port, the liquid waste outlet port, the separator body, the carrier gas inlet port, and the carrier gas outlet port are blown from quartz.

6. The fractional-volatilization separator as recited in claim 5, wherein the interior wall portion is frosted.

7. The fractional-volatilization separator as recited in claim 1, wherein the carrier gas outlet port is angled generally upwards when the generally longitudinal interior cavity is oriented in at least the upright position.

8. A system comprising:
   a fractional-volatilization separator including
       a liquid inlet port for receiving a liquid mixture, the liquid mixture containing a first component part and a second component part,
       a liquid waste outlet port for draining the liquid mixture after the first component part has been at least partially separated from the second component part of the liquid mixture,
       a separator body having an interior wall portion connecting the liquid inlet port and the liquid waste outlet port, the interior wall portion defining a generally longitudinal interior cavity and an aperture having a first diameter proximate to the liquid inlet port, the interior wall portion having a second diameter below the aperture when the fractional-volatilization separator is in an upright position, the interior wall portion transitioning outwardly from the first diameter to the second diameter at an angle,
       a carrier gas inlet port coupled with the separator body and connected to the generally longitudinal interior cavity for receiving a carrier gas, and
       a carrier gas outlet port coupled with the separator body and connected to the generally longitudinal interior cavity for expelling the carrier gas, the interior wall portion configured to cause the liquid mixture to flow from the liquid inlet port across the interior wall portion to the liquid waste outlet port to enhance evaporation of the first component part from the second component part as the carrier gas flows from the carrier gas inlet port to the carrier gas outlet port; and
   a pump coupled with the fractional-volatilization separator for supplying the liquid mixture to the liquid inlet port.

9. The system as recited in claim 8, wherein a first region of the interior wall portion disposed between the first diameter and the second diameter is oriented at an angle of between thirty degrees (30°) and sixty degrees (60°) from the horizontal when the generally longitudinal interior cavity is oriented in the upright position.

10. The system as recited in claim 8, wherein the liquid mixture comprises a mixture of at least one of a liquid and a gas, or a first liquid and a second liquid having different vapor pressures.

11. The system as recited in claim 8, further comprising:
    a first support attachment point connected to the separator body for coupling with a support for supporting the fractional-volatilization separator.

12. The system as recited in claim 8, wherein the liquid inlet port, the liquid waste outlet port, the separator body, the carrier gas inlet port, and the carrier gas outlet port are blown from quartz.

13. The system as recited in claim 12, wherein the interior wall portion is frosted.

14. The system as recited in claim 8, wherein the carrier gas outlet port is angled generally upwards when the generally longitudinal interior cavity is oriented in at least the upright position.

* * * * *